United States Patent
Kucklick (10) Patent No.: US 12,414,790 B2
(45) Date of Patent: *Sep. 16, 2025

(54) SYSTEM AND METHOD FOR DELIVERY AND POSITIONING OF SURGICAL IMPLANTS

(71) Applicant: SMITH & NEPHEW, INC., Memphis, TN (US)

(72) Inventor: Theodore R. Kucklick, Campbell, CA (US)

(73) Assignee: SMITH & NEPHEW, INC., Memphis, TN (US)

( * ) Notice: Subject to any disclaimer, the term of this patent is extended or adjusted under 35 U.S.C. 154(b) by 148 days.

This patent is subject to a terminal disclaimer.

(21) Appl. No.: 18/219,975

(22) Filed: Jul. 10, 2023

(65) Prior Publication Data
US 2023/0346412 A1    Nov. 2, 2023

Related U.S. Application Data (63) Continuation of application No. 17/143,804, filed on Jan. 7, 2021, now Pat. No. 12,127,756, which is a
(Continued)

(51) Int. Cl.
| | |
|---|---|
| *A61B 17/30* | (2006.01) |
| *A61B 17/29* | (2006.01) |
| *A61B 17/34* | (2006.01) |
| *A61B 17/56* | (2006.01) |
| *A61F 2/00* | (2006.01) |

(Continued)

(52) U.S. Cl.
CPC .............. *A61B 17/30* (2013.01); *A61B 17/29* (2013.01); *A61B 17/3468* (2013.01); *A61B 17/56* (2013.01); *A61F 2/0063* (2013.01); *F28C 1/02* (2013.01); *F28F 25/04* (2013.01);
(Continued)

(58) Field of Classification Search
CPC ........... A61F 2/0063; A61F 2002/0072; A61B 17/29; A61B 17/30; A61B 17/3468; A61B 17/2909; A61B 17/56; A61B 17/00234; A61B 17/00491; A61B 2017/2913; A61B 2017/292; A61B 2017/2937
See application file for complete search history.

(56) References Cited

U.S. PATENT DOCUMENTS

| | | | |
|---|---|---|---|
| 5,405,360 A * | 4/1995 | Tovey ................... | A61F 2/0063 606/151 |
| 5,957,939 A | 9/1999 | Heaven et al. | |

(Continued)

FOREIGN PATENT DOCUMENTS

| | | |
|---|---|---|
| WO | 2010/046893 A1 | 4/2010 |

OTHER PUBLICATIONS

International Preliminary Report on Patentability received for PCT Patent Application No. PCT/US2018/016673, mailed on May 8, 2019, 16 pages.

(Continued)

*Primary Examiner* — Diane D Yabut
(74) *Attorney, Agent, or Firm* — Seager, Tufte & Wickhem LLP (57) ABSTRACT

Systems and method for delivery and positioning of a sheet-like surgical implant to a target site including a means of deploying and orienting the sheet-like implant within the body.

19 Claims, 10 Drawing Sheets

Related U.S. Application Data continuation of application No. 16/530,731, filed on Aug. 2, 2019, now Pat. No. 10,912,579, which is a continuation-in-part of application No. PCT/US2018/016673, filed on Feb. 2, 2018.

(60) Provisional application No. 62/453,853, filed on Feb. 2, 2017.

(51) Int. Cl.
*F28C 1/02* (2006.01)
*F28F 25/04* (2006.01)
*F28F 25/06* (2006.01)

(52) U.S. Cl.
CPC ...... *F28F 25/06* (2013.01); *A61B 2017/2937* (2013.01); *A61F 2002/0072* (2013.01)

(56) References Cited

U.S. PATENT DOCUMENTS

| | | | |
|---|---|---|---|
| 6,015,426 A | 1/2000 | Griffiths | |
| 8,585,733 B2 | 11/2013 | Newell et al. | |
| 8,585,773 B1 | 11/2013 | Kucklick | |
| 2005/0283246 A1 | 12/2005 | Cauthen et al. | |
| 2008/0188874 A1 | 8/2008 | Henderson | |
| 2010/0106052 A1* | 4/2010 | Uznanski | A61B 17/22031 600/562 |
| 2010/0318121 A1* | 12/2010 | Levin | A61B 17/00491 606/213 |
| 2012/0116363 A1 | 5/2012 | Houser et al. | |
| 2012/0209401 A1* | 8/2012 | Euteneuer | A61F 2/0805 623/23.72 |
| 2015/0320543 A1 | 11/2015 | Zenz-Olson | |
| 2015/0335321 A1* | 11/2015 | Edelman | A61B 17/00491 623/2.11 |

OTHER PUBLICATIONS

International Search Report and Written Opinion received for PCT Patent Application No. PCT/US2018/016673, mailed on May 15, 2018, 16 pages.

* cited by examiner

SYSTEM AND METHOD FOR DELIVERY AND POSITIONING OF SURGICAL IMPLANTS

CROSS REFERENCE TO RELATED APPLICATIONS

This application is a continuation of U.S. patent application Ser. No. 17/143,804 filed Jan. 7, 2021, which is a continuation of U.S. patent application Ser. No. 16/530,731 filed on Aug. 2, 2019, which is a continuation-in-part of PCT/US2018/016673 filed on Feb. 2, 2018, which claims the benefit of U.S. Provisional Patent Application Ser. No. 62/453,853 filed on Feb. 2, 2017, the disclosures of which are incorporated herein by reference.

FIELD OF THE INVENTION

The inventions described below relate to the field of sheet-like surgical implants.

BACKGROUND OF THE INVENTION

Biologic constructs and other sheet-like surgical implants are growing rapidly in popularity for the repair of joint pathologies. "Biologic constructs" are a family of biologically derived implants to promote tissue growth or to patch and repair tissue defects and tears. These can be used in the repair of arthritic cartilage, the joining of tendons to bone and the bridging of degenerated rotator cuff in the shoulder. Biologic constructs, which include "regenerative tissue matrices" "acellular tissue matrices" or "collagen scaffolds" and other such substances, are small sheets or disks of flexible, engineered biomaterial, such as collagen or fibrin, decellularized dermal matrix crosslinked and sterilized xenograft tissues, and "platelet-rich-plasma" patches sometimes totally devoid of living cell material and sometimes loaded with active adjuncts such as biologic growth factors. Biologic constructs may also be tissue-engineered from mesenchymal stem cells. For the purposes of this application, the term biologic construct refers to any sheet-like or disc-like configuration of regenerative tissue matrix, acellular tissue matrices or collagen scaffolds, or similar materials suitable for placement within the body to promote healing.

Biologic constructs now occupy an increasingly important place in the orthopedic surgeons armamentarium. One of the key problems with biologic constructs is that the delivery instrumentation has not kept pace with advances in these implants. Positioning and alignment is particularly an issue. For example, the biologic constructs are often seeded with cells on only one side, and its very important to attach these implants with cells side down or they will not work. However, both sides look almost the same so its easy to make the mistake of placing them wrong side down.

SUMMARY

The systems and methods described below provide for delivery and positioning of sheet-like surgical implants adjacent to body tissue. The delivery system has a delivery tube assembly and any suitable drive mechanism such as a drive handle or robotic adapter or control system. The delivery tube assembly includes a pushrod shaft with resiliently expandable deployment arms positioned at the distal end of a pushrod shaft. The sheet-like implant is releasably secured to the deployment arms. The sheet-like implant is secured to the arms, and the assembled arms and implant are compressed to fit into the delivery tube, and the delivery tube is inserted into the body.

The system is modular, with separable drive handle (or drive mechanism) and delivery tube assembly. The delivery system can be equipped with fluid or gas management through the delivery tube assembly. The delivery tube assembly provides for articulation, via either flexible or hinged deployment, which is especially useful in hernia repair.

This system may be used for both biologic construct delivery in arthroscopy as well as other sheet and scaffold repair procedures. The system may be used for any soft tissue repair procedure where a synthetic or biologic patch is used, such as joint repair or hernia repair. A method for positioning the sheet-like surgical implant adjacent to body tissue is also described.

DETAILED DESCRIPTION OF THE INVENTIONS

Figure 1A:
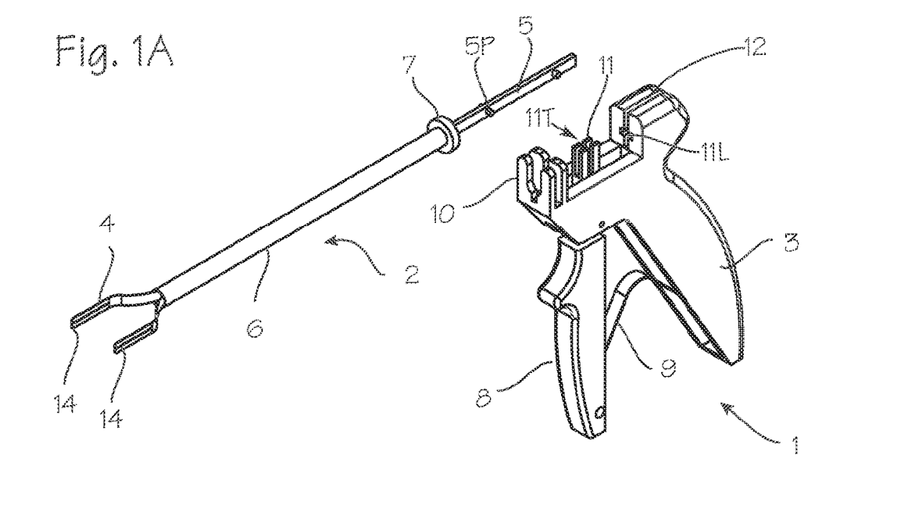
FIGS. 1A and 1B illustrate the sheet-like implant delivery system.
Figure 1B:
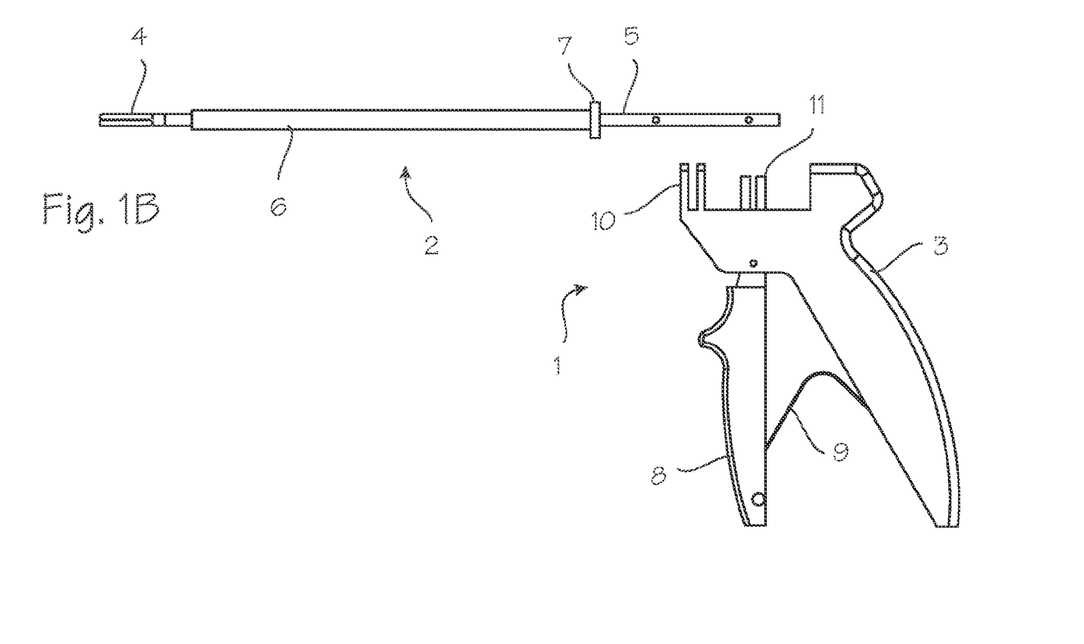

FIGS. 1A and 1B illustrate a sheet-like implant delivery system 1 comprising a delivery tube assembly 2 and a drive handle 3. The delivery tube assembly 2 comprises a pair of deployment arms 4 attached to the distal end of a pushrod shaft 5. The pushrod shaft 5 is slidably disposed within a delivery tube 6. The delivery tube 6 has a retainer feature (flange 7) for engagement with the drive handle 3. The deployment arms 4 are retractable, and may be retracted proximally within the delivery tube 6, and are resiliently biased toward the open configuration shown in FIG. 1A, and may be compressed and drawn down to a closed configuration, smaller than the lumen of the delivery tube, when pulled into the delivery tube 6.

The drive handle 3 (or pistol grip) comprises a deployment trigger 8, a spring 9, a retainer slot 10, a drive yoke 11 and a guide slot 12. Engagement between the delivery tube assembly and the drive handle is created by slipping the pushrod shaft into the longitudinally oriented push rod guide slot 11L and pushing the pin 5P into the transverse slot 11T of the yoke, and slipping the delivery tube retainer feature (flange 7) into the drive handle retainer slot 10. As illustrated, the delivery tube assembly is releasably attached to the drive handle (that is, the delivery tube assembly can be quickly attached to and detached from the drive handle without using tools such as screw drivers or wrenches).

The delivery tube assembly 2 allows for a range of implant sizes in one system usable with a common drive handle 3. For example, the deployment arms 4 may be smaller or larger, depending on the size of the implant. The device may be provided in kits, with a single handle and several delivery tube assemblies with deployment arms and/or biologic patches of different sizes, which may be chosen for use by a surgeon during surgery, to suit the actual natural or surgically altered anatomy of a particular patient. The diameter of the delivery tube can be larger or smaller to accommodate the size of the deployment arms. The delivery tube assembly 2 and the drive handle 3 may be disposable or reusable.

Figures 2A, 2B:
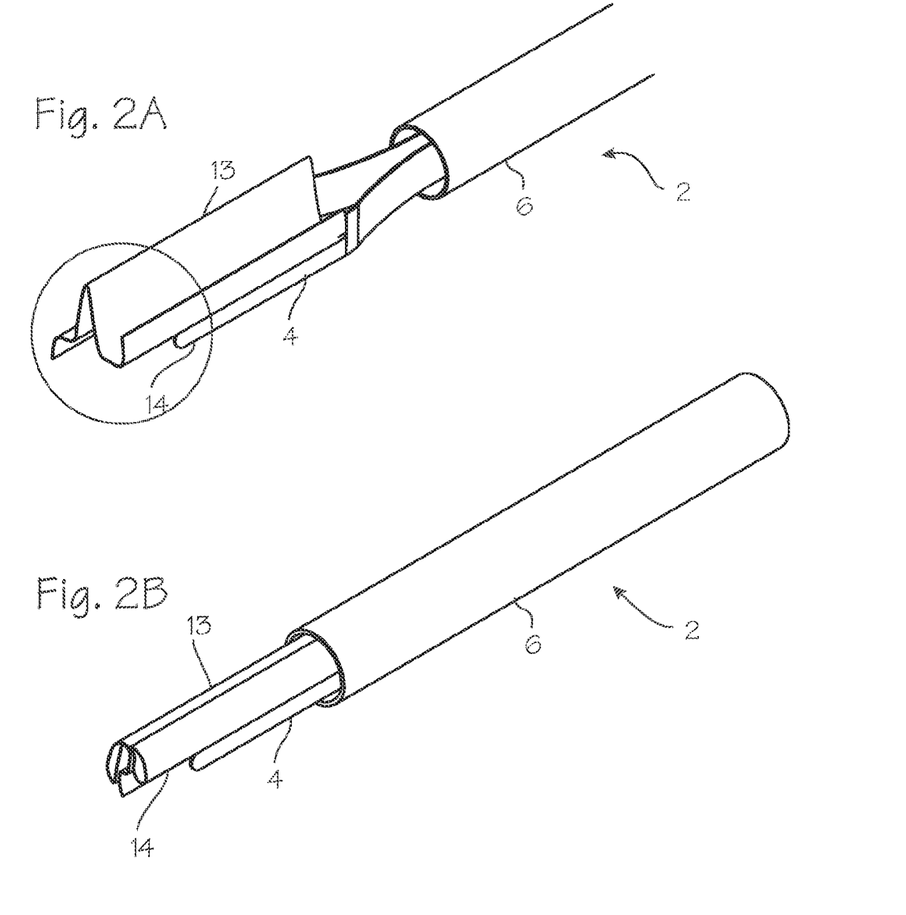
FIGS. 2A through 2F illustrate detailed views of the sheet-like implant folded on the deployment arms.
Figure 2C:
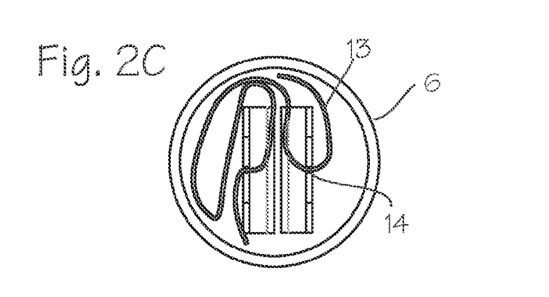

FIGS. 2A through 2C show a close up of the deployment arms 4 with an attached sheet-like implant 13. The sheet-like implant 13 is inserted in a slot 14 within each deployment arm 4, slidably engaging the slots and thus detachably secured to the deployment arms 4. The longitudinal slot 14 runs substantially the length of the deployment arm and each slot is sized to hold a portion of the sheet-like implant by a friction fit between the deployment arm slots and the sheet-like implant. Clamps may also be used to attach the implant to the arms. The sheet-like implant 13 is folded or rolled as shown in FIGS. 2A through 2D and compressed and loaded within the delivery tube 6 of the delivery system 1. The deployment arms 4 and pushrod shaft 5 are positioned within the delivery tube 6. The pushrod shaft 5, with the components assembled, is pulled proximally through the delivery tube 6 prior to delivery into a surgical space. The sheet-like implant folds when the user retracts the deployment arms. Alternatively, the user may manually fold and roll the implant around the deployment arms prior to retraction within the delivery tube.

Figure 2D:
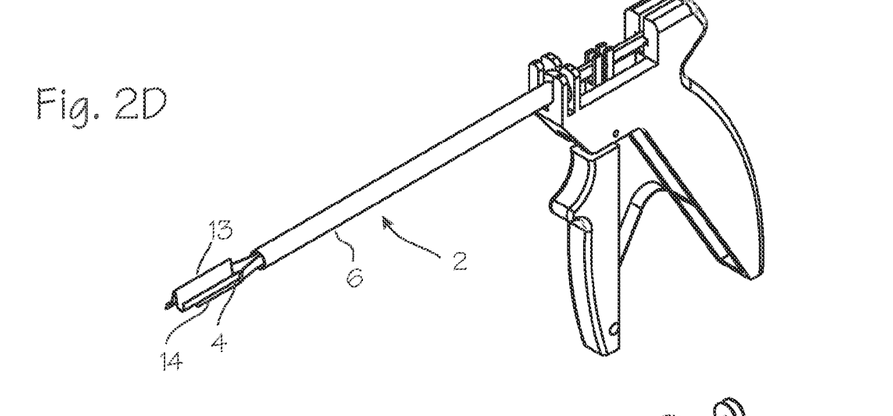
Figure 2E:
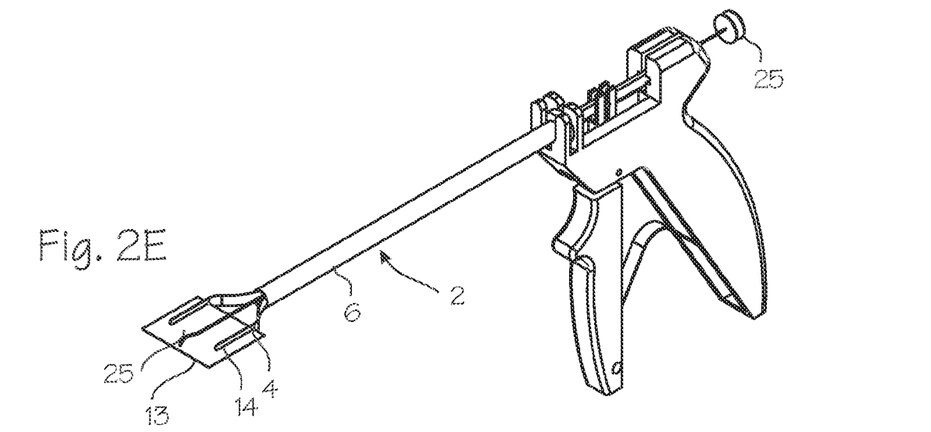
Figure 2F:
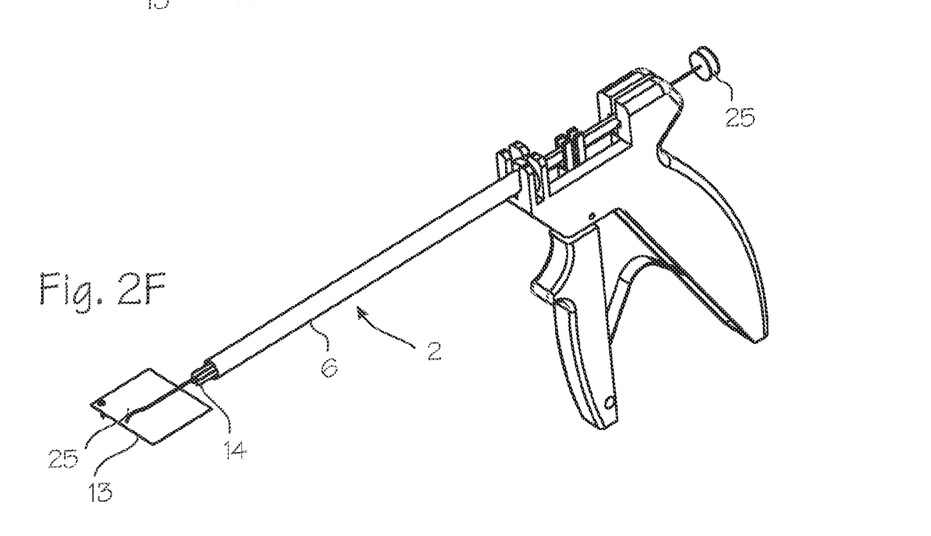

As shown in FIGS. 2D through 2F, deployment of the implant is performed by manipulating the trigger 8 in the drive handle 3 to extend the pushrod 5 distally from the delivery tube 6 (or pull the delivery tube proximally, depending on the construction of the handle). Upon full deployment distally from the delivery tube, the implant is drawn flat by the resilient expansion of the deployment arms 4. The sheet-like implant is positioned flat in the desired position and sutured or staked in place (with other instruments if necessary) or glued in place. Upon positioning and release of the implant, the arms are retracted proximally through the delivery tube and the delivery system is withdrawn from the surgical site.

The deployment arms are made of a resilient material (spring metal, nitinol, or plastic) such that they spring open when deployed distally from the distal end of the delivery tube. A first deployment arm and a second deployment arm each have a proximal and a distal end with the proximal end of each arm coupled to the distal end of the pushrod shaft. The first and second deployment arms are moveable between a closed position and an open position wherein in the closed position the arms extend generally in the longitudinal direction and in pivoting to the open position the distal end of each arm moves in a generally transverse direction to spread the sheet-like implant. The distal segments of the arms are arranged in roughly a parallel fashion and a proximal segment of each arm bends toward the center of the tube to join the pushrod shaft at their proximal ends. An optional holder 25, as shown in FIGS. 2E and 2F, may be provided to help hold the implant in place while the deployment arms are retracted. The holder shaft may be disposed in a lumen of the pushrod shaft or the delivery tube, and longitudinally translatable within the lumen, extendable distally to the sheet-like implant and operable to hold the implant in place.

The delivery tube is rotatable around the pushrod shaft. This allows the user to manipulate the deployment arms and thus, place the sheet-like implant in a desirable position. For example, the user can orient a biologic construct so that the correct side (for example seeded with cells) is placed correctly on the tissue to be treated.

Figure 3A:
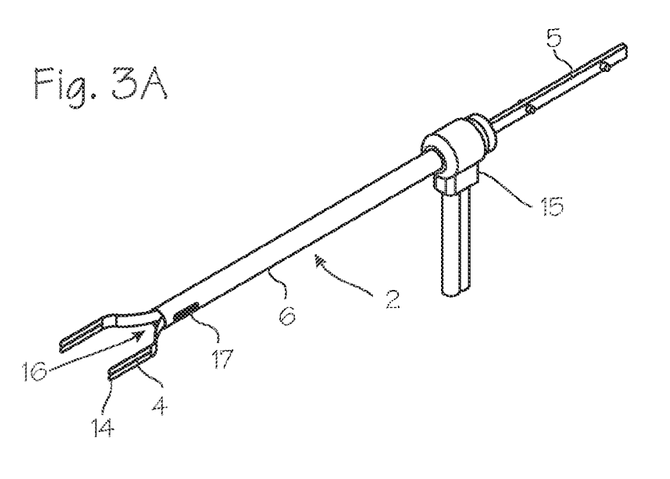
FIGS. 3A and 3B illustrate a sheet-like implant delivery system with integrated fluid management.
Figure 3B:
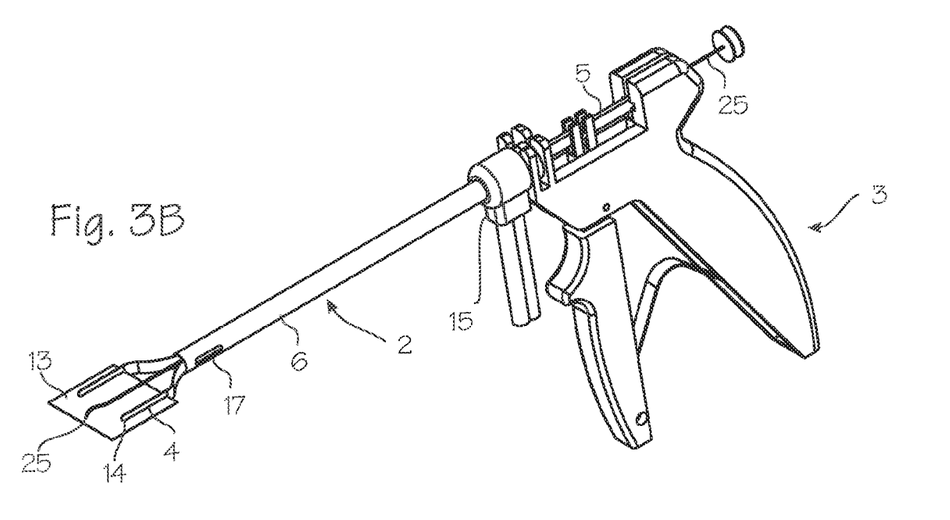

FIGS. 3A and 3B show the implant delivery system with integrated fluid management. A fluid manifold 15 is attached in fluid communication with the implant delivery tube assembly. The fluid manifold provides for fluid inflow and fluid outflow. Fluid inflow enters in through the distal end 16 of the device between the deployment arms and fluid outflow exits from an aperture 17 in the sidewall of the delivery tube. Separate channels may be provided for inflow and outflow. The fluid can be saline (as in a standard arthroscopic technique) or gas (to be compatible with a tissue adhesive such as fibrin glue).

Figures 4A, 4B:
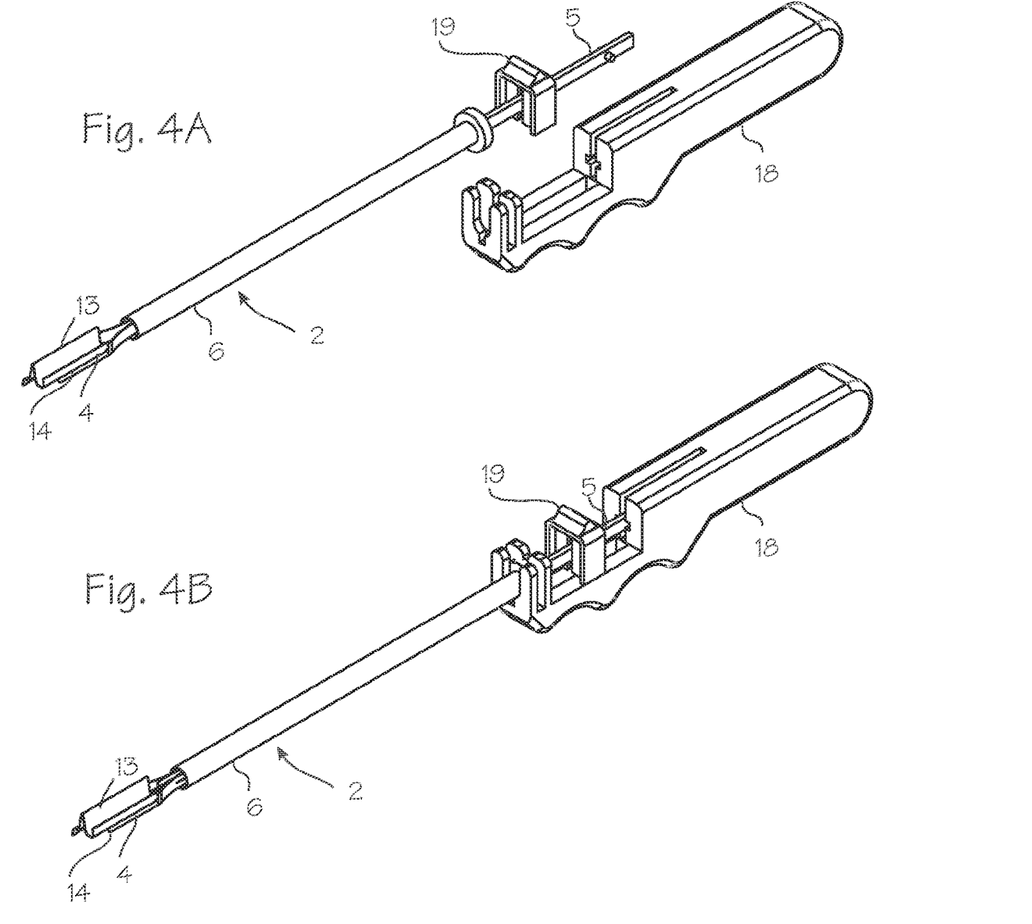
FIGS. 4A through 4C illustrate a sheet-like implant delivery system with a straight handle and slider actuator.
Figure 4C:
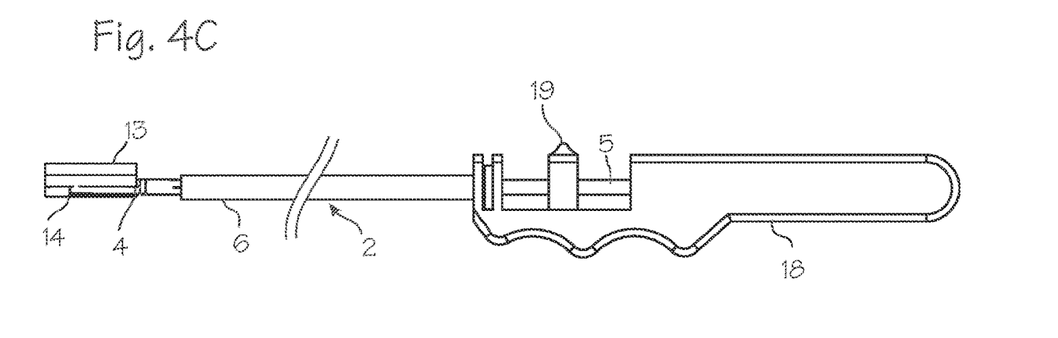

The implant delivery system can have a straight handle 18 with slide actuator 19 as shown in FIGS. 4A through 4C. The pushrod shaft is drawn proximally and extended distally by the user correspondingly manipulating the slider actuator in a proximal and distal direction.

Figure 5A:
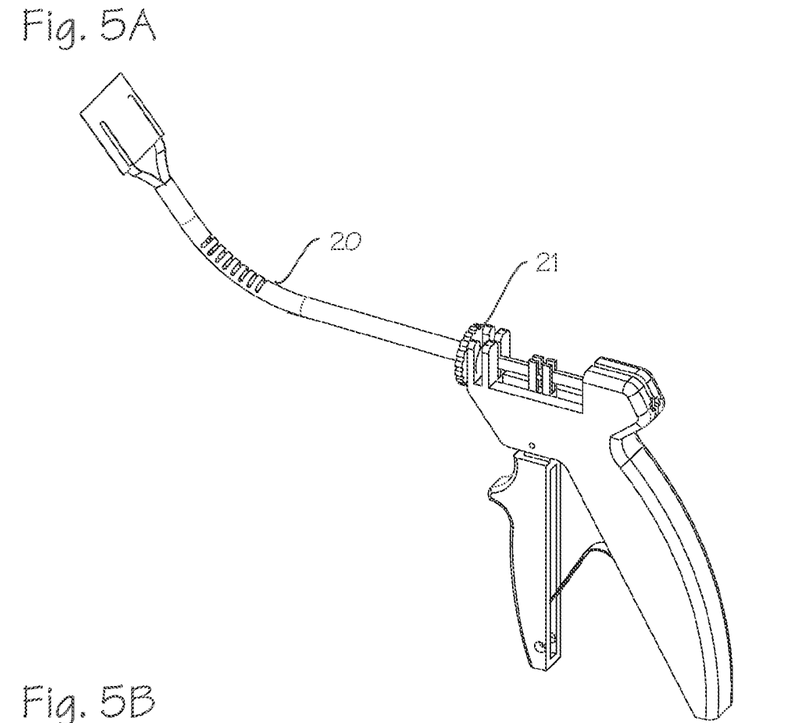
FIGS. 5A through 5D illustrate sheet-like implant delivery systems with articulation.
Figure 5B:
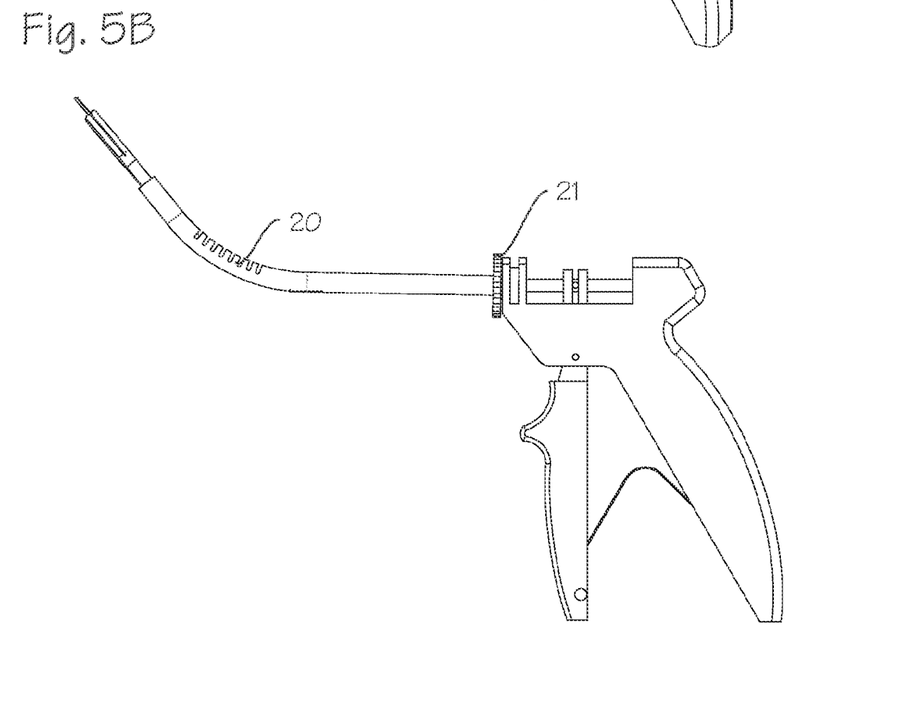
Figure 5C:
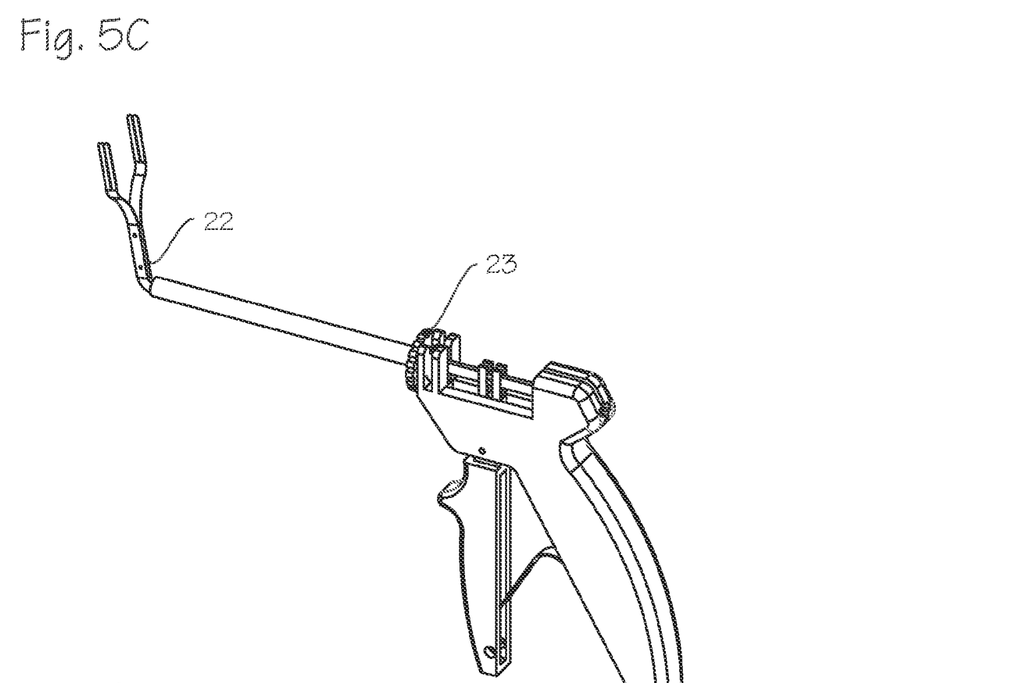
Figure 5D:
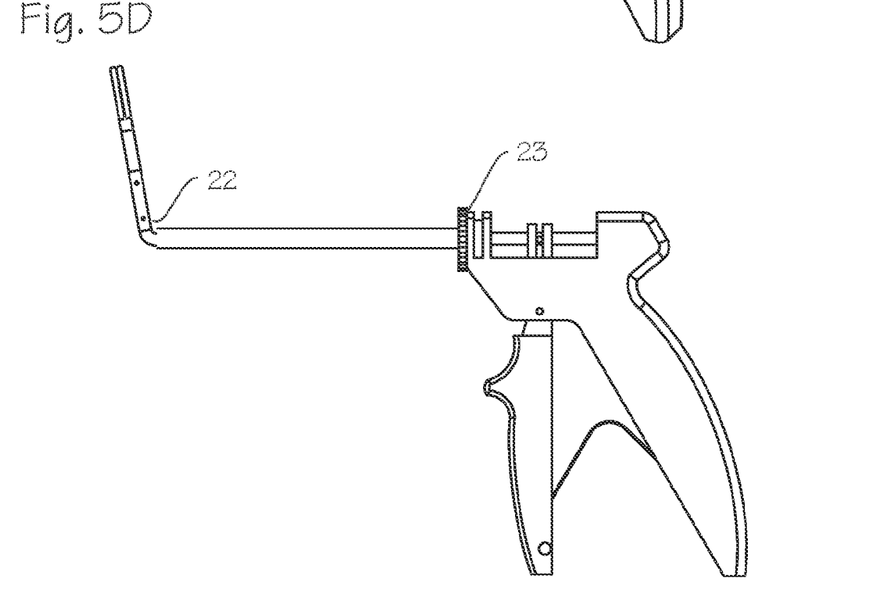

FIGS. 5A through 5D show an implant delivery system with articulation. FIGS. 5A and 5B show a delivery system where the pushrod shaft is a flexible of bendable shaft 20. Flex control is performed via a rotating wheel 21 controlled by the drive handle. FIGS. 5C and 5D show a hinged pushrod 22 controlled by a rotating wheel 22.

Figure 6:
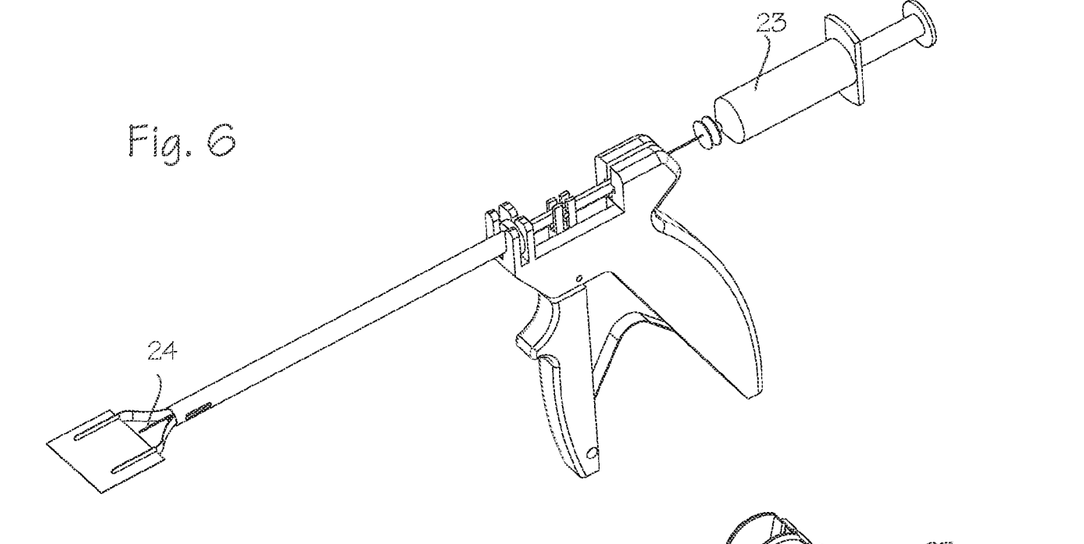
FIG. 6 illustrates a sheet-like implant delivery system with integrated fluent delivery.

FIG. 6 shows the implant delivery system with a system for delivering a fluent medication to the surgical site (for example, tissue adhesives, stem cells, platelet rich plasma (PRP) or medications). Fluent medications are injected from the fluid source in fluid communication with the delivery tube assembly using a pump or syringe 23 operably connected to a delivery needle or catheter 24, which is inserted through the delivery tube assembly. The fluent delivery can be used, for example, to place a tissue adhesive under the biologic construct for fixation. The fluent delivery can apply stem cells or PRP to the side of the biologic construct contacting the tissue (tendon, cartilage) to be treated.

Figure 7A:
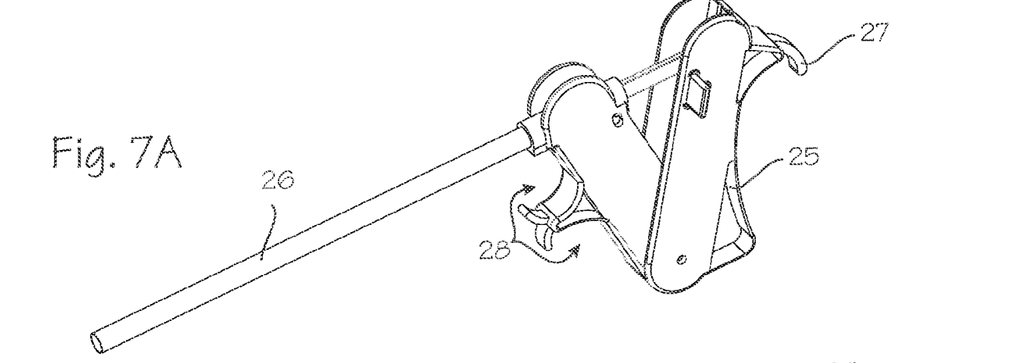
FIGS. 7A and 7B illustrate a sheet-like implant delivery system with thumb and finger loop handle.
Figure 7B:
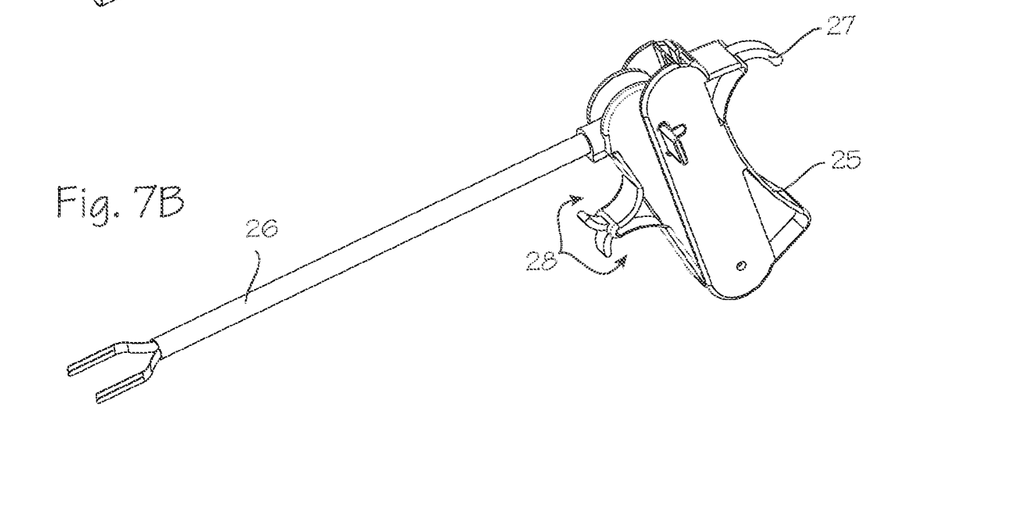

FIGS. 7A and 7B show an alternate drive handle 25 and delivery tube assembly 26. The drive handle has thumb 27 and finger loops 28, which allow the user to exert reverse force on the drive handle to retract the delivery arms back into the delivery tube.

In use, the surgeon delivers the implant to a joint within the body of a patient by creating an arthroscopic workspace around the joint and inserting a cannula through the skin of the patient proximate the arthroscopic workspace. The surgeon attaches the implant 13 to the deployment arms 4 and retracts the pushrod shaft 5 with the sheet attached to the deployment arms such that the deployment arms and sheet fit through the delivery tube within the cannula. The surgeon inserts the delivery tube assembly through the cannula and into the arthroscopic workspace. The surgeon pulls the drive handle deployment trigger, thus pushing the pushrod shaft 5 in a distal direction to extend the deployment arms and sheet within the workspace and positioning the sheet proximate an intended site of implantation.

The surgeon then secures the sheet to body tissue within the workspace. The implant is secured with staples, sutures, clips or other means, with a separate instrument. The implant may also be secured with a tissue adhesive deliverable through the delivery tube assembly (as shown in FIG. 6) or a separate instrument. Once the implant is essentially staked in place, the surgeon releases the implant from the deployment arms by sliding the arms proximally, whereupon the implant is slidably released from the arms, and the arms withdrawn proximally into the delivery tube. The surgeon retracts the pushrod shaft within the delivery tube and removes the implant delivery system from the workspace.

Figure 8:
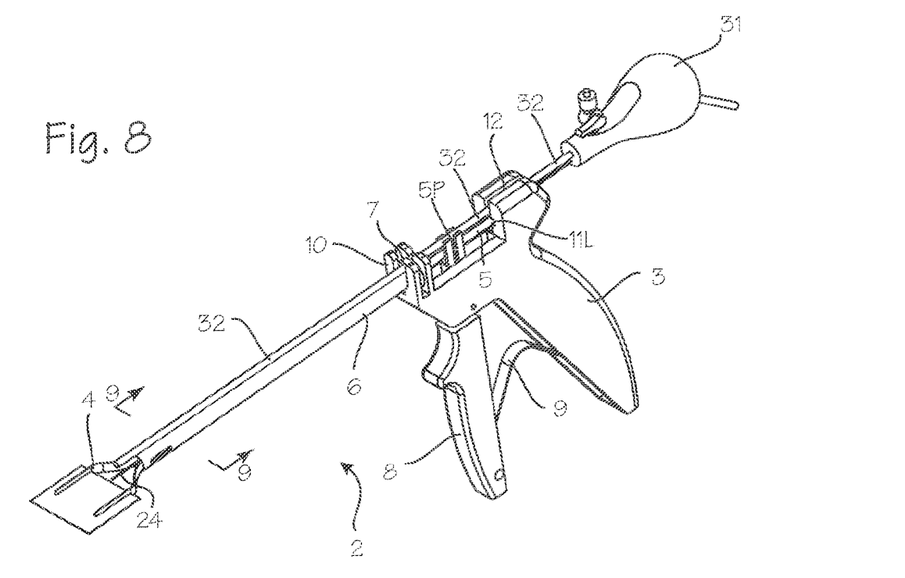
FIG. 8 illustrates a sheet-like implant delivery system with integrated endoscope.

FIG. 8 shows the implant delivery system with an integrated endoscope or camera 31. This allows for visualization of the biologic patch 13 through a single portal or a reduced number of portals. The endoscope 31 can be conventional, reusable, analog or digital and is operably connected to the proximal end of the pushrod shaft 5 and may extend through a working channel, a side lumen, or a tube attached on the outside of delivery tube 6, with the distal end of the endoscope extending out through the distal end of the delivery tube 6 into the surgical space. Alternatively, the delivery tube assembly 2 may have a built in camera that is disposable with the unit 2. FIG. 8 shows the system components as described in FIG. 1A, including the delivery tube assembly 2, deployment arms 4, pushrod shaft 5, delivery tube 6 and drive handle 3.

Figure 9A:
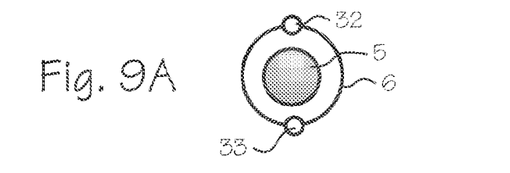
FIGS. 9A through 9C are cross sectional views of the distal end of the delivery system of FIG. 8 taken along 9-9.
Figure 9B:
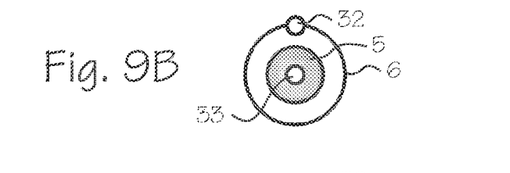
Figure 9C:
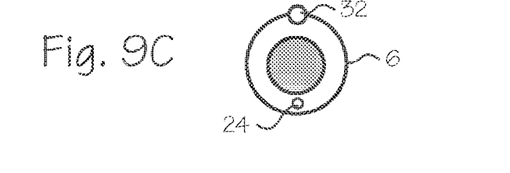

The delivery tube assembly 2 may comprise one or two working channels. FIG. 9A shows, for example, a first working channel 32 and a second working channel 33 disposed on the outer surface of the delivery tube assembly 2. The first working channel may accommodate the endoscope slidably disposed within the working channel and the second working channel operably connected to a delivery needle or catheter 24. FIG. 9B shows a first working channel disposed on the outer surface of the delivery tube and a second working channel disposed within the pushrod shaft 5. The first working channel may accommodate the endoscope slidably disposed within the working channel and the second working channel operably connected to a delivery needle or catheter 24. FIG. 9C shows one working channel disposed on the outer surface of the delivery tube assembly and a delivery needle or catheter 24 disposed within a side lumen within the wall of the delivery tube 6.

Figures 10A, 10B:
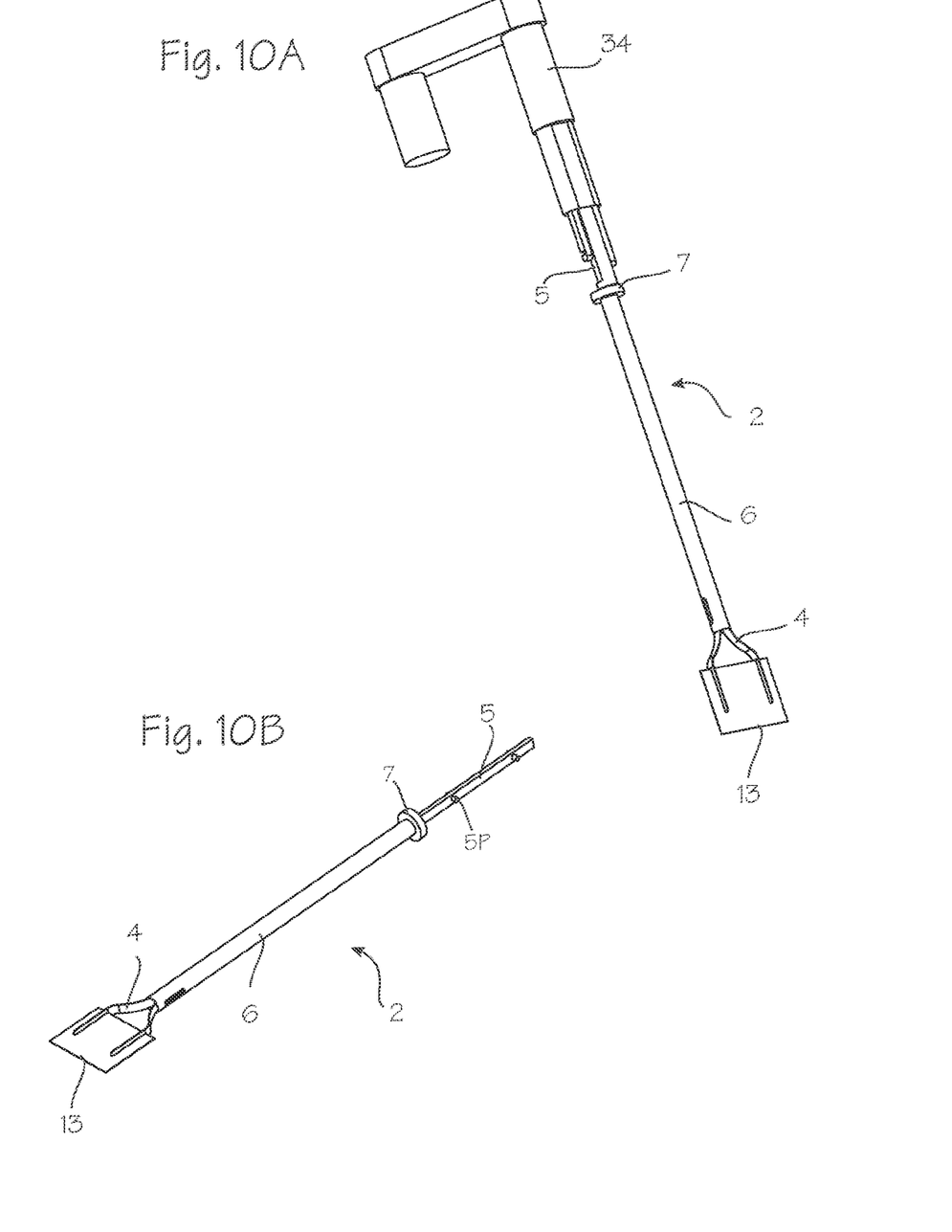
FIGS. 10A and 10B illustrate a sheet-like implant delivery system with a drive mechanism for use with a robotic control system adapter.

FIGS. 10A and 10B show the delivery system with robotic control system adapter 34. FIGS. 10A and 10B show the system components as described in FIG. 1A, including the delivery tube assembly 2, deployment arms 4, pushrod shaft 5, pins 5P, delivery tube 6, retainer feature 7. The delivery tube assembly 2 may be used with a variety of drive systems such as manual handles as previously shown, and may also be used with a robotic control system adapter 34. The delivery tube assembly 2 snaps into a holder and has features that engage with a motion controlled driver to advance the deployment arms 4, deploy the implant 13, attach the implant 13 to tissue with mechanical fasteners, sutures or adhesive, remove the implant from the arms 4, and withdraw the delivery tube 6 from the surgical work space. The delivery tube assembly 2 can be releasably attached and removed from a robotic surgery system. Deployment of the biologic sheet spreader is actuated by the robotic system, and the delivery tube assembly 2 has attachment features that allow the robotic actuator to push the rod and arms 4 within the outer tube 6, and to deploy the sheet biologic 13 into the surgical space. The robotic system may have a robotic actuator that can control the deployment of the biologic sheet, as well as the deflection of the pushrod shaft 5. The arms 4 may also have a non-stick coating.

While the preferred embodiments of the devices and methods have been described in reference to the environment in which they were developed, they are merely illustrative of the principles of the inventions. The system is modular, with separable drive handle and delivery tube assembly. Alternatively, the system can be assembled as a single unit. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

What is claimed is:

1. A delivery system for delivering a sheet-like implant to a surgical site, said system comprising:
   a delivery tube having a distal end, a proximal end, and a lumen extending from the proximal end to the distal end;
   an elongate shaft slideably positioned through the lumen of the delivery tube;
   a handle assembly coupled to the proximal end of the delivery tube for selectively actuating the elongate shaft relative to the delivery tube;
   a pair of deployment arms attached to a distal end of the elongate shaft;
   a sheet-like implant coupled to the pair of deployment arms;
   wherein manipulation of the handle assembly causes translation of the elongate shaft within the lumen of the delivery tube to deploy the pair of deployment arms from the distal end of the delivery tube with the sheet-like implant spanning between the pair of deployment arms; and
   a fluid delivery channel extending through the elongate shaft from a proximal end of the handle assembly to the distal end of the delivery tube.

2. The delivery system of claim 1, wherein each deployment arm of the pair of deployment arms includes a longitudinal slot extending along a length of the deployment arm.

3. The delivery system of claim 2, wherein the sheet-like implant is frictionally held in the longitudinal slots of the pair of deployment arms.

4. The delivery system of claim 1, wherein the sheet-like implant extends between the plurality of deployment arms with no intervening structure therebetween.

5. The delivery system of claim 1, wherein the delivery tube further includes a working channel disposed within a wall of the delivery tube.

6. The delivery system of claim 1, wherein the delivery tube further includes a working channel disposed along an outer edge of the delivery tube.

7. The delivery fluid delivery system of claim 1, wherein the fluid delivery channel extends past the distal end of the delivery tube.

8. The delivery system of claim 7, wherein a distal end of the fluid delivery channel is disposed near the deployment arms and is configured for depositing fluid onto the sheet-like implant.

9. The fluid delivery system of claim 1, further comprising a syringe connectable to a proximal end of the fluid delivery channel.

10. A delivery system for delivering a sheet-like implant to a surgical site, said system comprising:
    a delivery tube having a distal end, a proximal end, and a lumen extending from the proximal end to the distal end;
    an elongate shaft slideably positioned through the lumen of the delivery tube;

a handle assembly coupled to the proximal end of the delivery tube for selectively actuating the elongate shaft relative to the delivery tube;

a pair of deployment arms attached to a distal end of the elongate shaft;

wherein the pair of deployment arms is resiliently biased to an open configuration wider than the lumen of the delivery tube, and compressible to a closed configuration in which the pair of deployment arms are disposed within the lumen of the delivery tube;

a sheet-like implant coupled to the pair of deployment arms;

wherein manipulation of the handle assembly causes translation of the elongate shaft within the lumen of the delivery tube to deploy the pair of deployment arms from the distal end of the delivery tube with the sheet-like implant spanning between the pair of deployment arms;

wherein the sheet-like implant is in a folded configuration within the lumen of the delivery tube, and upon deployment of the deployment arms, the sheet-like implant is spread to an unfolded configuration;

a fluid delivery channel extending through the delivery tube to the distal end of the delivery tube; and a syringe connectible to the proximal end of the handle and in fluid communication with the fluid delivery channel;

wherein manipulation of the syringe causes fluid to be dispensed from the distal end of the fluid delivery channel onto the sheet-like implant spanning between the pair of deployment arms.

11. The delivery system of claim 10, wherein manipulation of the handle assembly causes retraction of the elongate shaft proximally within the delivery tube, bringing the deployment arms to the compressed state within the delivery tube.

12. The delivery system of claim 11, wherein retraction of the elongate shaft releases the sheet-like implant into the surgical site.

13. The delivery system of claim 10, wherein the sheet-like implant extends between the plurality of deployment arms with no intervening structure therebetween.

14. The delivery system of claim 10, wherein the pair of deployment arms are parallel to one another along a longitudinal axis of the delivery tube assembly in both the open and closed configurations.

15. The delivery system of claim 10, wherein the sheet-like implant is held in longitudinal slots of the pair of deployment arms.

16. The delivery system of claim 10, wherein the fluid delivery channel extends within the elongate shaft.

17. The delivery system of claim 10, wherein the delivery tube is a flexible shaft.

18. A method for delivering a sheet-like implant to a surgical site, the method comprising;

advancing a delivery system for delivering a sheet-like implant to a surgical site, said system comprising:
a delivery tube having a distal end, a proximal end, and a lumen extending from the proximal end to the distal end;
an elongate shaft slideably positioned through the lumen of the delivery tube;
a handle assembly coupled to the proximal end of the delivery tube for selectively actuating the elongate shaft relative to the delivery tube;
a pair of deployment arms attached to a distal end of the elongate shaft;
wherein the pair of deployment arms is resiliently biased to an open configuration wider than the lumen of the delivery tube, and compressible to a closed configuration in which the pair of deployment arms are disposed within the lumen of the delivery tube;
a sheet-like implant coupled to the pair of deployment arms;
a fluid delivery channel extending through the delivery tube elongate shaft from a proximal end of the handle assembly to the distal end of the delivery tube; and
a syringe, connectible to the proximal end of the handle and in fluid communication with the fluid delivery channel;

manipulating the handle assembly to translate the elongate shaft within the lumen of the delivery tube to deploy the pair of deployment arms from the distal end of the delivery tube with the sheet-like implant spanning between the pair of deployment arms, wherein upon deployment of the pair of deployment arms, the sheet-like implant is spread to an unfolded configuration;

manipulating the syringe to dispense a fluid from the distal end of the fluid delivery channel onto the sheet-like implant spanning between the pair of deployment arms; and attaching the sheet-like implant to body tissue within the surgical site.

19. The delivery method of claim 18, wherein the fluid is a tissue adhesive and the sheet-like implant is attached to the body tissue by the tissue adhesive.

* * * * *